United States Patent
Damren et al.

(10) Patent No.: US 11,708,555 B2
(45) Date of Patent: Jul. 25, 2023

(54) SYSTEM, METHOD AND APPARATUS FOR DRAINING A BIOREACTOR VESSEL

(71) Applicant: GLOBAL LIFE SCIENCES SOLUTIONS USA LLC, Marlborough, MA (US)

(72) Inventors: Richard Damren, Marlborough, MA (US); Colin Tuohey, Medway, MA (US); Ralph Stankowski, Westborough, MA (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 445 days.

(21) Appl. No.: 16/426,028

(22) Filed: May 30, 2019

(65) Prior Publication Data

US 2020/0377841 A1    Dec. 3, 2020

(51) Int. Cl.
*C12M 1/26* (2006.01)
*C12M 1/00* (2006.01)

(52) U.S. Cl.
CPC ............ *C12M 33/04* (2013.01); *C12M 23/14* (2013.01); *C12M 23/26* (2013.01); *C12M 29/00* (2013.01)

(58) Field of Classification Search
CPC ....... B67D 7/36; B67D 7/0294; F16K 31/445; F16K 31/508; C12M 23/28; C12M 33/04; C12M 23/14; C12M 23/26; C12M 29/00
See application file for complete search history.

(56) References Cited

U.S. PATENT DOCUMENTS

| | | | |
|---|---|---|---|
| 2,653,792 A * | 9/1953 | Sacchini | F16L 29/00 137/540 |
| 7,766,304 B2 * | 8/2010 | Phillips | A61M 39/02 604/905 |
| 9,044,718 B2 | 6/2015 | Ludwig et al. | |
| 9,475,686 B2 | 10/2016 | Tuohey et al. | |
| 10,190,084 B2 * | 1/2019 | Baskar | C12M 29/20 |
| 2003/0036192 A1 * | 2/2003 | Singh | C12M 27/16 435/297.2 |
| 2011/0020922 A1 * | 1/2011 | Wuenn | C12M 29/04 435/297.1 |
| 2012/0260608 A1 | 10/2012 | Pethe et al. | |
| 2013/0167960 A1 * | 7/2013 | Pethe | B01F 15/0085 137/798 |

(Continued)

FOREIGN PATENT DOCUMENTS

EP    2503320 A2    9/2012

OTHER PUBLICATIONS

International Search Report and Written Opinion from related PCT application No. PCT/EP2020/064652 dated Sep. 15, 2020.

*Primary Examiner* — William H. Beisner
*Assistant Examiner* — Danielle B Henkel
(74) *Attorney, Agent, or Firm* — Grogan, Tuccillo & Vanderleeden, LLP

(57) ABSTRACT

An apparatus for draining a bioreactor vessel includes a tubular body portion having an interior passageway, and at least one aperture in the tubular body portion providing for fluid communication with the interior passageway, the tubular body portion being configured for positioning at a bottom of a vessel, and a suction tube having a first end configured for fluid coupling with the tubular body portion, and a second end configured for fluid coupling with a port in a sidewall of the vessel.

11 Claims, 9 Drawing Sheets

(56) References Cited

U.S. PATENT DOCUMENTS

| | | | |
|---|---|---|---|
| 2014/0011270 A1* | 1/2014 | Chotteau | C12M 27/20 |
| | | | 435/326 |
| 2014/0103077 A1 | 4/2014 | Zumbrum et al. | |
| 2017/0191016 A1 | 7/2017 | Lee et al. | |
| 2019/0367859 A1* | 12/2019 | Gagne | B01F 7/06 |
| 2020/0102204 A1 | 4/2020 | Saukkonen | |

* cited by examiner

SYSTEM, METHOD AND APPARATUS FOR DRAINING A BIOREACTOR VESSEL

BACKGROUND

Technical Field

Embodiments of the invention relate generally to bioprocessing systems and methods and, more particularly, to a system, method and apparatus for draining a bioreactor vessel.

Discussion of Art

In the biopharmaceutical industry, increasingly, single-use or disposable containers or flexible bags are used. Such containers can be flexible or collapsible plastic bags that are supported by an outer rigid structure such as a stainless steel shell, referred to herein as a "vessel." The use of sterilized, disposable bags eliminates the time-consuming step of cleaning the steel bioreactor vessel and reduces the chance of contamination. In use, the bag is filled with the desired fluid for mixing, and an impeller disposed within the bag (driven by a magnetic drive system or motor positioned outside the vessel) is used to mix the fluid. Depending on the fluid being processed, the system may include a number of fluid lines and different sensors, probes and ports coupled with the bag for monitoring, analytics, sampling, and fluid transfer. For example, a plurality of ports may typically be located at the front of the bag and accessible through an opening in the sidewall of the vessel, which provide connection points for sensors, probes and/or fluid sampling lines. In addition, a harvest port or drain line fitting is typically located at the bottom of the disposable bag and is configured for insertion through an opening in the bottom of the vessel, allowing for a harvest line to be connected to the bag for harvesting and draining of the bag after the bioprocess is complete.

Currently available single-use bioreactors often utilize hose barb or similar fittings that are welded to the bag film as entry and exit points for conveyance of fluid, including for the draining of fluid from the bottom of the flexible bag. The drain line fitting generally has a tubular portion that provides for one-way fluid flow out of the bottom of the flexible bag (either via a valve integrated with the drain line fitting or the harvest line). These type of bottom-draining flexible bioprocessing bags require users to reach under the bioreactor vessel to manipulate the drain line and valves during installation, draining and bag removal, which can be cumbersome from an ergonomic and ease of use standpoint.

In view of the above, there is a need for devices and methods that facilitate draining of a bioreactor vessel in a manner that is more convenient and ergonomic for an operator.

BRIEF DESCRIPTION

In an embodiment, an apparatus for draining a bioreactor vessel is provided. The apparatus includes a tubular body portion having an interior passageway, and at least one aperture in the tubular body portion providing for fluid communication with the interior passageway, the tubular body portion being configured for positioning at a bottom of a vessel, and a suction tube having a first end configured for fluid coupling with the tubular body portion, and a second end configured for fluid coupling with a port in a sidewall of the vessel.

In another embodiment, a bioprocessing system is provided. The bioprocessing system includes a vessel. a flexible bioprocessing bag positionable within the vessel, and an apparatus for draining the flexible bioprocessing bag positioned at a bottom of the flexible bioprocessing bag. The apparatus includes a tubular body portion having an interior passageway, and at least one aperture in the tubular body portion providing for fluid communication with the interior passageway, the tubular body portion being configured for positioning at a bottom of a flexible bioprocessing bag. The apparatus also includes a suction tube having a first end configured for fluid coupling with the tubular body portion, and a second end configured for fluid coupling with a port in a sidewall of the flexible bioprocessing bag.

In yet another embodiment, a method of draining a flexible bioprocessing bag is provided. The method includes the steps of arranging a suction tube interior to a flexible bioprocessing bag such that a first end of the suction tube is connected to a suction drain device attached to a bottom of the flexible bioprocessing bag and a second end of the suction tube is connected to a port in a sidewall of the flexible bioprocessing bag, changing a state of the suction drain device to place an interior of the flexible bioprocessing bag in fluid communication with the suction tube, and activating a pump to draw a fluid from the interior of the flexible bioprocessing bag into the suction tube and out of the flexible bioprocessing bag through the port in the sidewall of the flexible bioprocessing bag.

In another embodiment, a bioprocessing apparatus is provided. The bioprocessing apparatus includes a flexible bioprocessing bag, and an apparatus for draining the flexible bioprocessing bag positioned at a bottom of the flexible bioprocessing bag. The apparatus includes a tubular body portion having an interior passageway, and at least one aperture in the tubular body portion providing for fluid communication with the interior passageway, the tubular body portion being configured for positioning at a bottom of a flexible bioprocessing bag. The apparatus also includes a suction tube having a first end configured for fluid coupling with the tubular body portion, and a second end configured for fluid coupling with a port in a sidewall of the flexible bioprocessing bag.

DRAWINGS

The present invention will be better understood from reading the following description of non-limiting embodiments, with reference to the attached drawings, wherein below:

DETAILED DESCRIPTION

Figure 1:
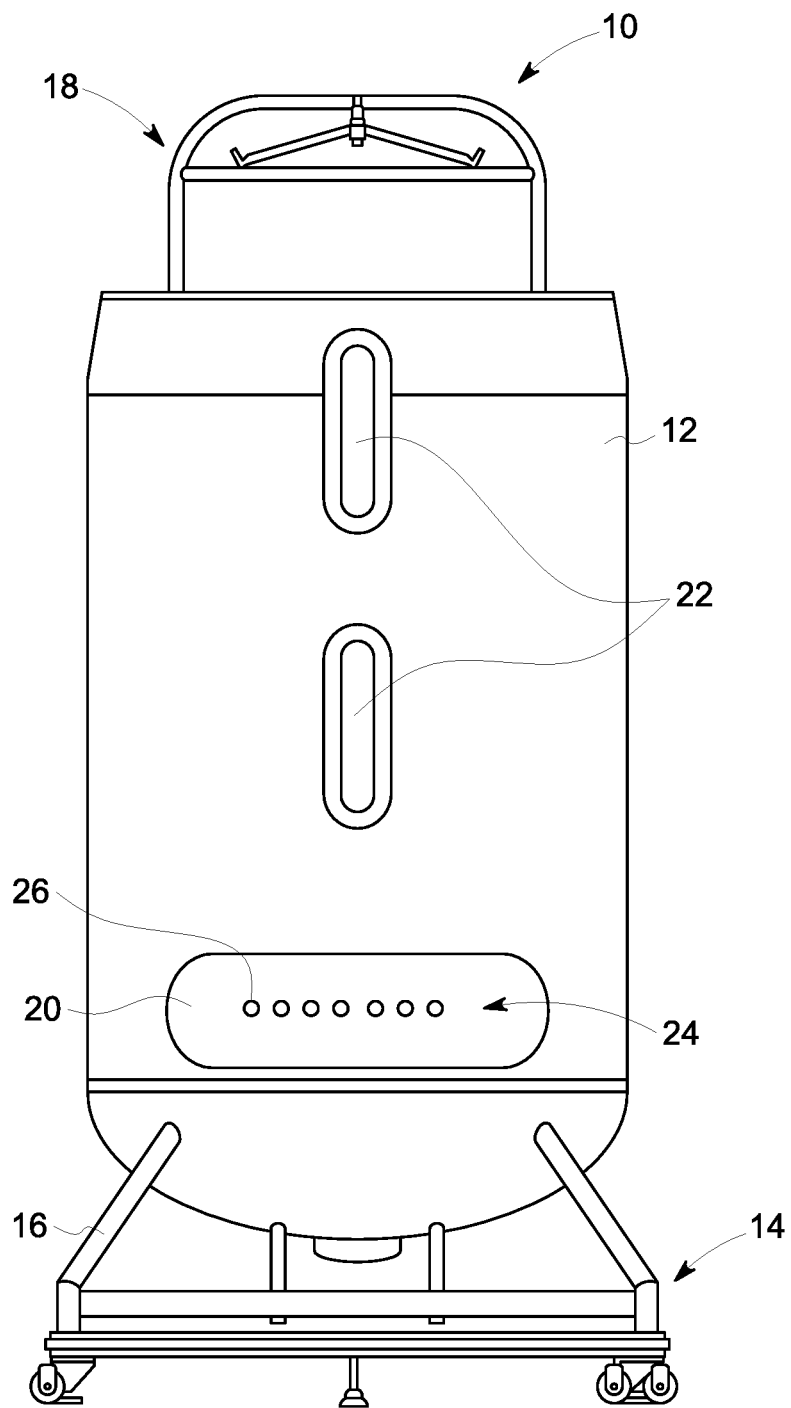
FIG. 1 is a front elevational view of a bioreactor system according to an embodiment of the invention.

Reference will be made below in detail to exemplary embodiments of the invention, examples of which are illustrated in the accompanying drawings. Wherever possible, the same reference characters used throughout the drawings refer to the same or like parts.

As used herein, the term "flexible" or "collapsible" refers to a structure or material that is pliable, or capable of being bent without breaking, and may also refer to a material that is compressible or expandable. An example of a flexible structure is a bag formed of polyethylene film. The terms "rigid" and "semi-rigid" are used herein interchangeably to describe structures that are "non-collapsible," that is to say structures that do not fold, collapse, or otherwise deform under normal forces to substantially reduce their elongate dimension. Depending on the context, "semi-rigid" can also denote a structure that is more flexible than a "rigid" element, e.g., a bendable tube or conduit, but still one that does not collapse longitudinally under normal conditions and forces.

A "vessel," as the term is used herein, means a flexible bag, a flexible container, a semi-rigid container, a rigid container, or a flexible or semi-rigid tubing, as the case may be. The term "vessel" as used herein is intended to encompass bioreactor vessels having a wall or a portion of a wall that is flexible or semi-rigid, single use flexible bags, as well as other containers or conduits commonly used in biological or biochemical processing, including, for example, cell culture/purification systems, mixing systems, media/buffer preparation systems, and filtration/purification systems, e.g., chromatography and tangential flow filter systems, and their associated flow paths. As used herein, the term "bag" means a flexible or semi-rigid container or vessel used, for example, as a bioreactor or mixer for the contents within.

Embodiments of the invention provide various devices for draining the contents of a bioreactor vessel and, more particularly, from a single-use, flexible bioprocessing bag of a bioprocessing system. While embodiments of the invention are described in connection with flexible, single-use bioprocessing bags for use in the biopharmaceutical industry, it is contemplated that the draining devices, systems and methods described herein can likewise be used for the draining and/or sampling of the contents of containers, tubing and vessels, more generally.

With reference to FIG. 1, a bioreactor system 10 according to an embodiment of the invention is illustrated. The bioreactor system 10 includes a generally rigid bioreactor vessel or support structure 12 mounted atop a base 14 having a plurality of legs 16. The vessel 12 may be formed, for example, from stainless steel, polymers, composites, glass, or other metals, and may be cylindrical in shape, although other shapes may also be utilized without departing from the broader aspects of the invention. The vessel 12 may be outfitted with a lift assembly 18 that provides support to a single-use, flexible bag 20 disposed within the vessel 12. The vessel 12 may include one or more sight windows 22, which allows one to view a fluid level within the flexible bag 20, as well as a window 24 positioned at a lower area of the vessel 12 in a sidewall of the vessel 12. The window 24 allows access to the interior of the vessel 12 for insertion and positioning of various sensors and probes (not shown) within the flexible bag 20, and for connecting one or more fluid lines to the flexible bag 20 for fluids, gases, and the like, to be added or withdrawn from the flexible bag 20. Sensors/probes and controls for monitoring and controlling important process parameters include any one or more, and combinations of: temperature, pressure, pH, dissolved oxygen (DO), dissolved carbon dioxide ($pCO_2$), mixing rate, and gas flow rate, for example. The vessel 12 may also include an opening in the bottom thereof, which has typically been utilized for connecting drain or discharge tubing to the flexible bag 20 via welding or other connectors for draining and/or harvesting the contents of the flexible bag 20.

The flexible bioreactor bag 20 may include a suction drain device or apparatus according to one of various embodiments of the invention described hereinafter, and the bag and suction drain device may be presterilized, e.g. by gamma radiation and offered or sold as a product for use in a bioreactor vessel, e.g., bioreactor vessel 12. The bag 20 can then suitably be equipped with aseptic connectors (e.g., GE Healthcare ReadyMate™ connectors, or with closed lengths of tubing for connection by sterile welding).

Figure 2:
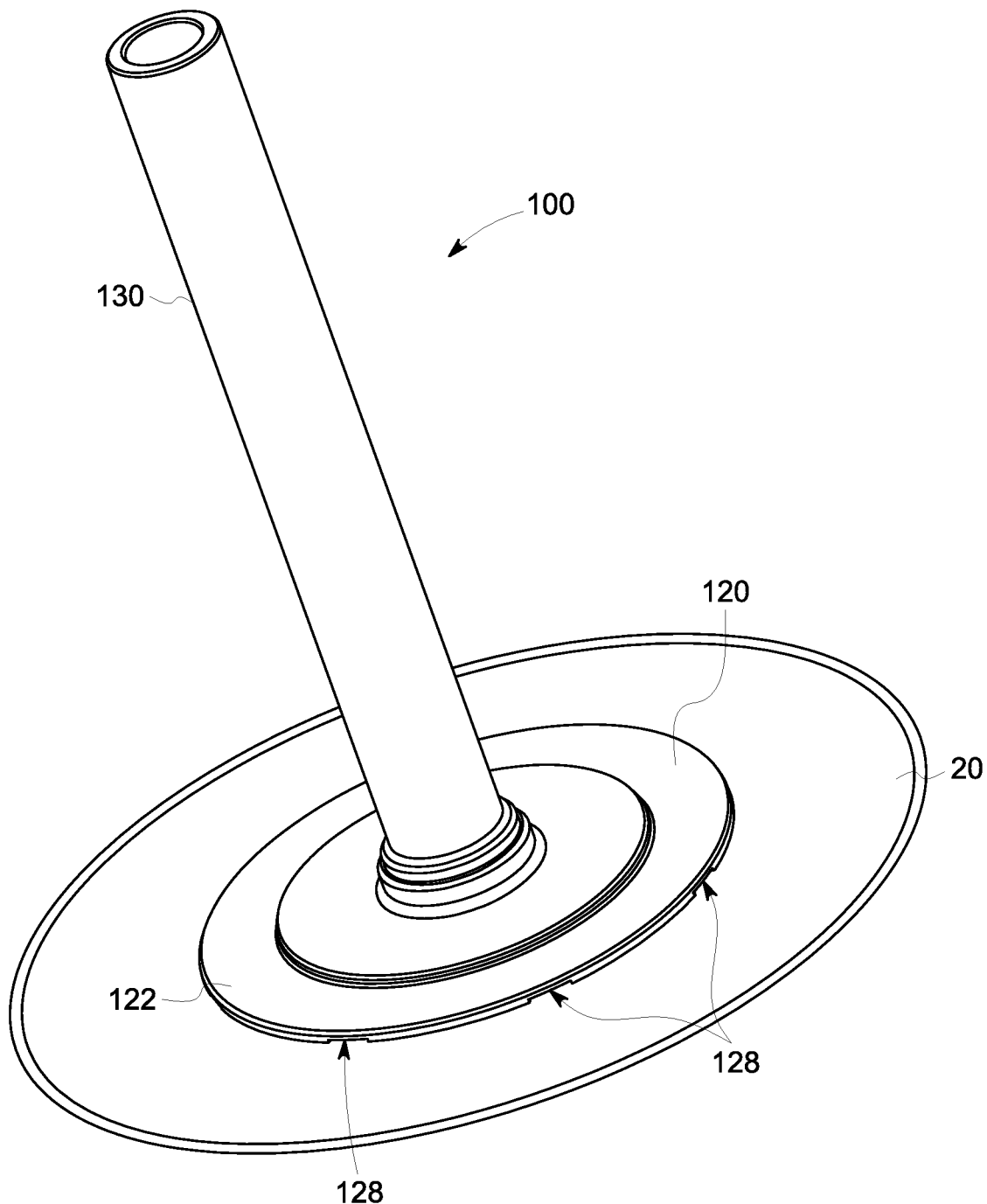
FIG. 2 is a perspective view of an apparatus for draining a bioreactor vessel, according to an embodiment of the invention.
Figure 3:
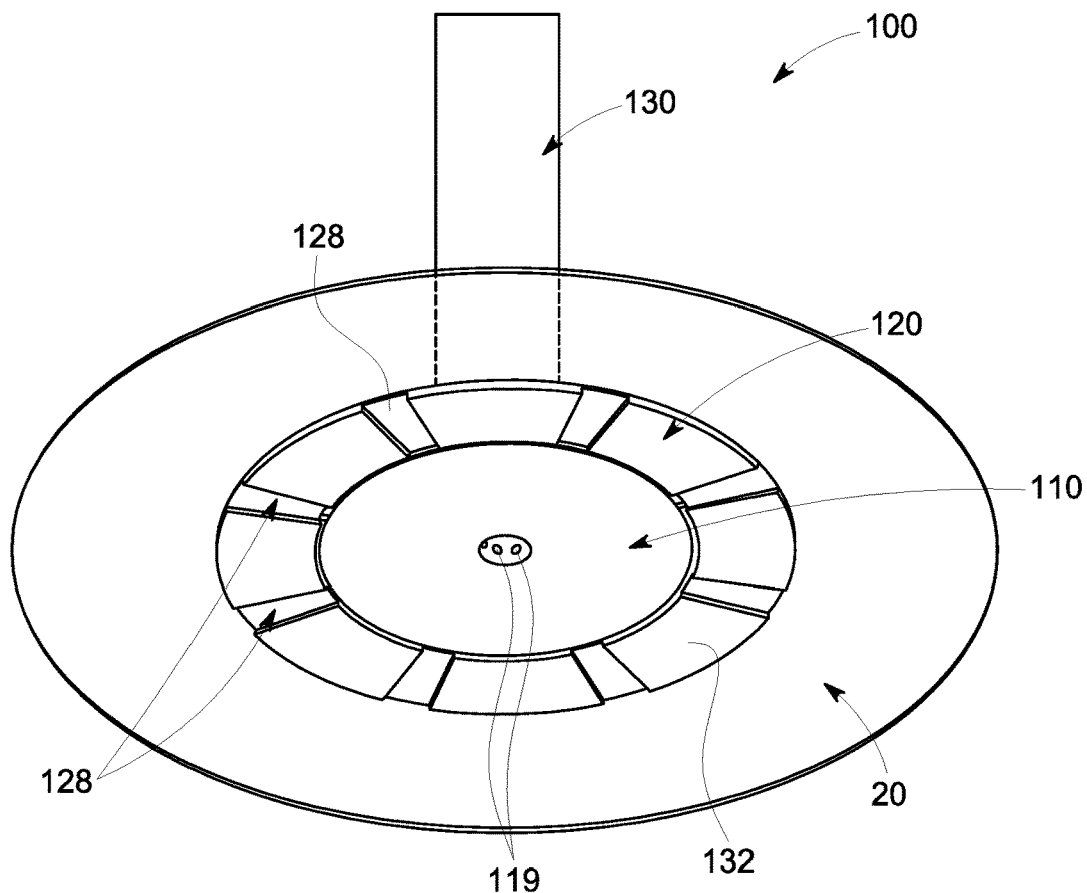
FIG. 3 is a bottom, perspective view of the apparatus of FIG. 2.
Figure 4:
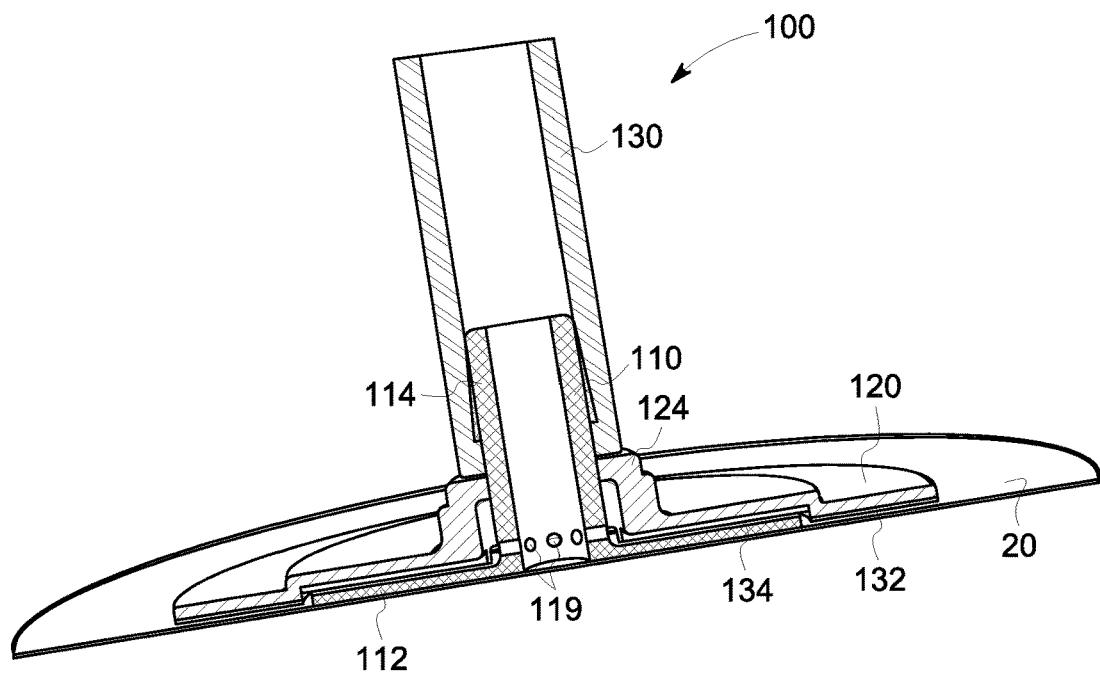
FIG. 4 is a perspective, cross-sectional view of the apparatus of FIG. 2.

FIGS. 2-4 illustrate one configuration of a suction drain device or apparatus 100 that can be integrated with the flexible bag 20 for draining of the contents of the bag 20. As shown therein, the apparatus 100 includes a drain port 110 affixed to the interior of the flexible bag 20 at the bottom of the flexible bag 20. The drain port 110 may be affixed to a low point of the flexible bag 20 as it sits within the vessel 12, which facilitates draining of the entire contents of the flexible bag, as discussed in detail hereinafter. The drain port 110 may be welded to the bottom of the flexible bag 20, although other means of attachment such as adhesives and the like may also be utilized without departing from the broader aspects of the invention. The apparatus 100 also includes a drain flange 120 that is received atop the drain port 110, and a suction tube 130 that is coupled the drain port 110, as discussed in detail hereinafter.

Figure 5:
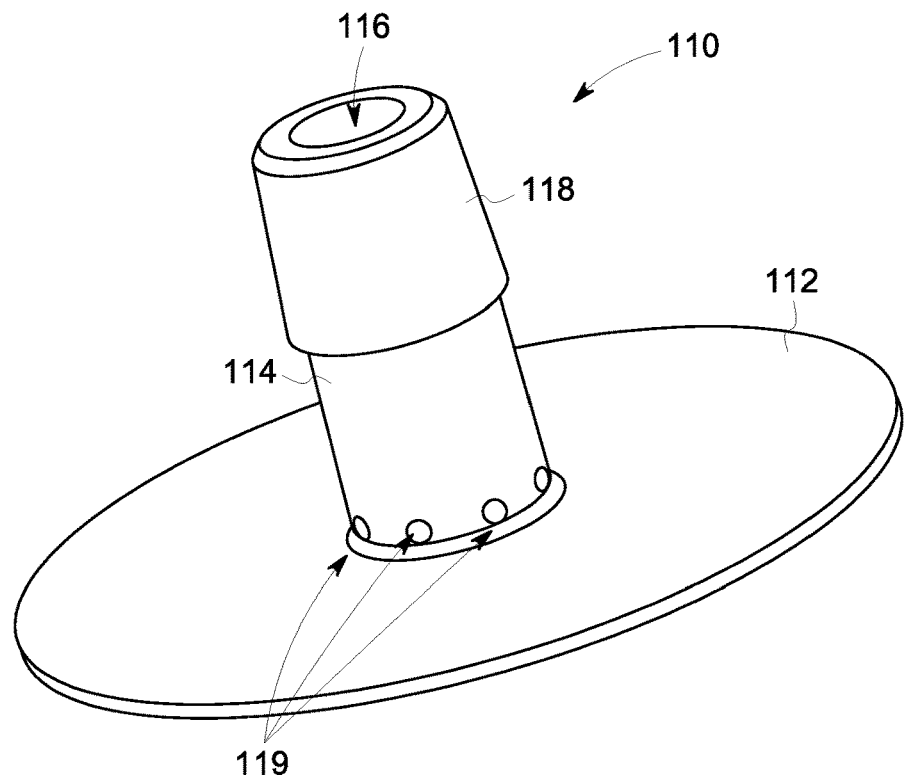
FIG. 5 is a perspective view of a drain port of the apparatus of FIG. 2.

With specific reference to FIG. 5, the drain port 110 includes a generally disc-shaped flange 112 and a tubular body portion 114 connected to, or integrally formed with, the flange 112. The tubular body portion 114 extends upwardly, and substantially perpendicularly, from the flange 112 and defines an interior passageway 116 extending from a distal end of the body portion 114 to the underside of the flange 112. The body portion 114 may be configured with a hose barb connector portion 118 for receiving and securing the suction tube 130 to the drain port 110, as best shown in FIG. 5. It is contemplated, however, that other connection means may also be utilized, such as hose clamps, welding, adhesives and the like, without departing from the broader aspects of the invention. The body portion 114 of the drain port 110 includes an array of apertures that extend through the tubular body portion 114 and are in fluid communication with the interior passageway 116. As shown in FIG. 5, in an embodiment, the apertures 119 are located at a lower area of the tubular body portion 114 just above the top surface of the flange 112 and are arranged at regularly spaced intervals around the periphery of the tubular body portion 114. Internal ribbing within the tubular portion 114 may be present to strengthen the tubular body portion 114.

Figure 6:
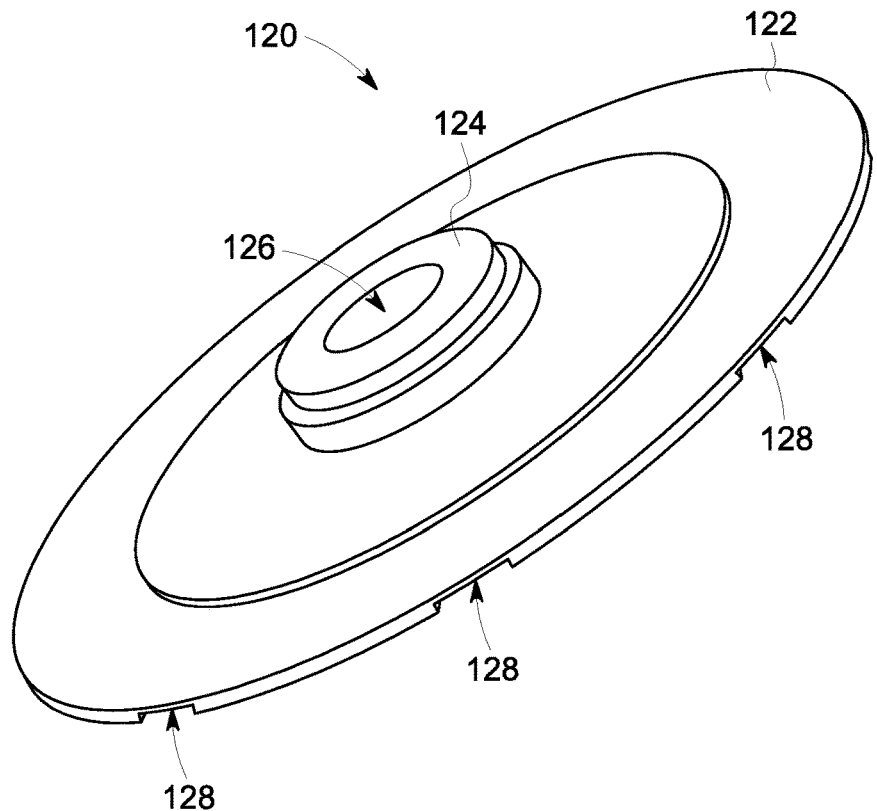
FIG. 6 is a top perspective view of a drain flange of the apparatus of FIG. 2.
Figure 7:
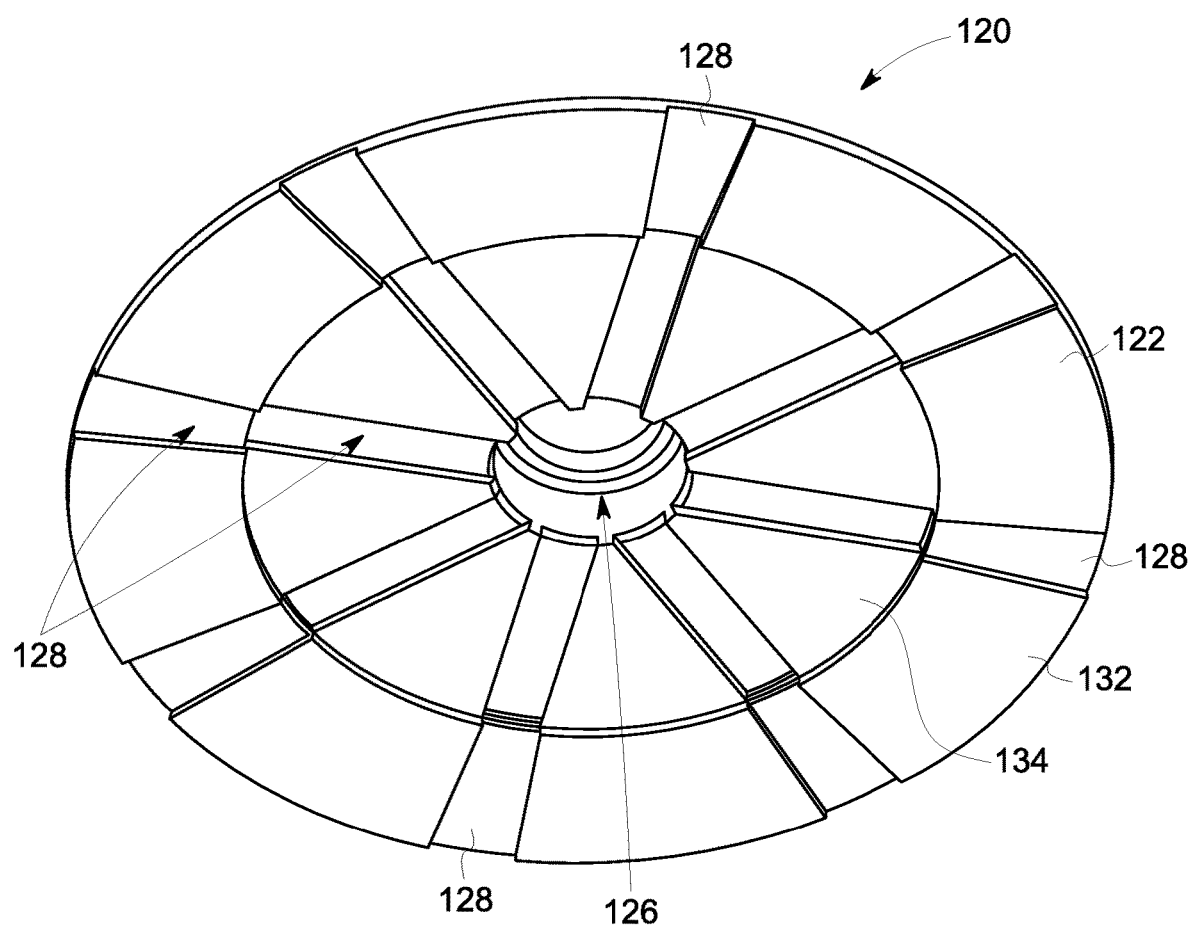
FIG. 7 is a bottom perspective view of the drain flange of FIG. 2.

Turning now to FIGS. 6 and 7, more detailed views of the drain flange 120 are shown. The drain flange 120 includes an annular or disc-shaped body portion 122 and a neck 124 that extends upwardly, and substantially perpendicularly, from the body portion 122. The neck 124 defines an interior passageway 126 extending from a distal end of the neck 124 to the underside of the body portion 122. As best shown in FIG. 7, the bottom surface of drain flange 120 is defined by a downward-facing, outer annular surface 132 and a downward-facing inner annular surface 134. The inner annular surface 134 is recessed with respect to the outer annular surface 132, such that the inner annular surface 134 lies in a plane that is parallel to, but spaced vertically from, a plane within which the outer annular surface 132 lies. That is, in an embodiment, the outer annular surface 132 and the inner annular surface 134 are not coplanar. In an embodiment, however, the bottom surface of the drain flange 120 may lie in a single plane.

As further shown in FIG. 7, the bottom surface of the drain flange 120 includes a plurality of radial grooves or channels 128 that extend from an outer periphery of the body portion 122 to the passageway 126. These channels provide for fluid communication between the passageway 126 and the interior of the flexible bag 20, as described hereinafter. In an embodiment, the drain flange 120 is formed from a thin, flexible material such as silicone.

Referring once again to FIG. 4, the flange 112 of the drain port 110 is secured to the bottom, interior surface of the flexible bag 20 in the manner described above. The drain flange 120 is then placed over the drain port 110 such that the tubular body portion 114 of the drain port 110 extends through the neck 124 of the drain flange 120. The interior of the neck 124 and the tubular body portion 114 are dimensioned such that a seal is created between the interior walls of the neck 124 and the outer periphery of the tubular body portion 114. A first end of the suction tube 130 is then connected to the tubular body portion 114 of the drain port 110 via the hose barb connector 118 or other connection means. In an embodiment, the suction tube 130 may be formed from silicone or other materials common in the art.

Figure 8:
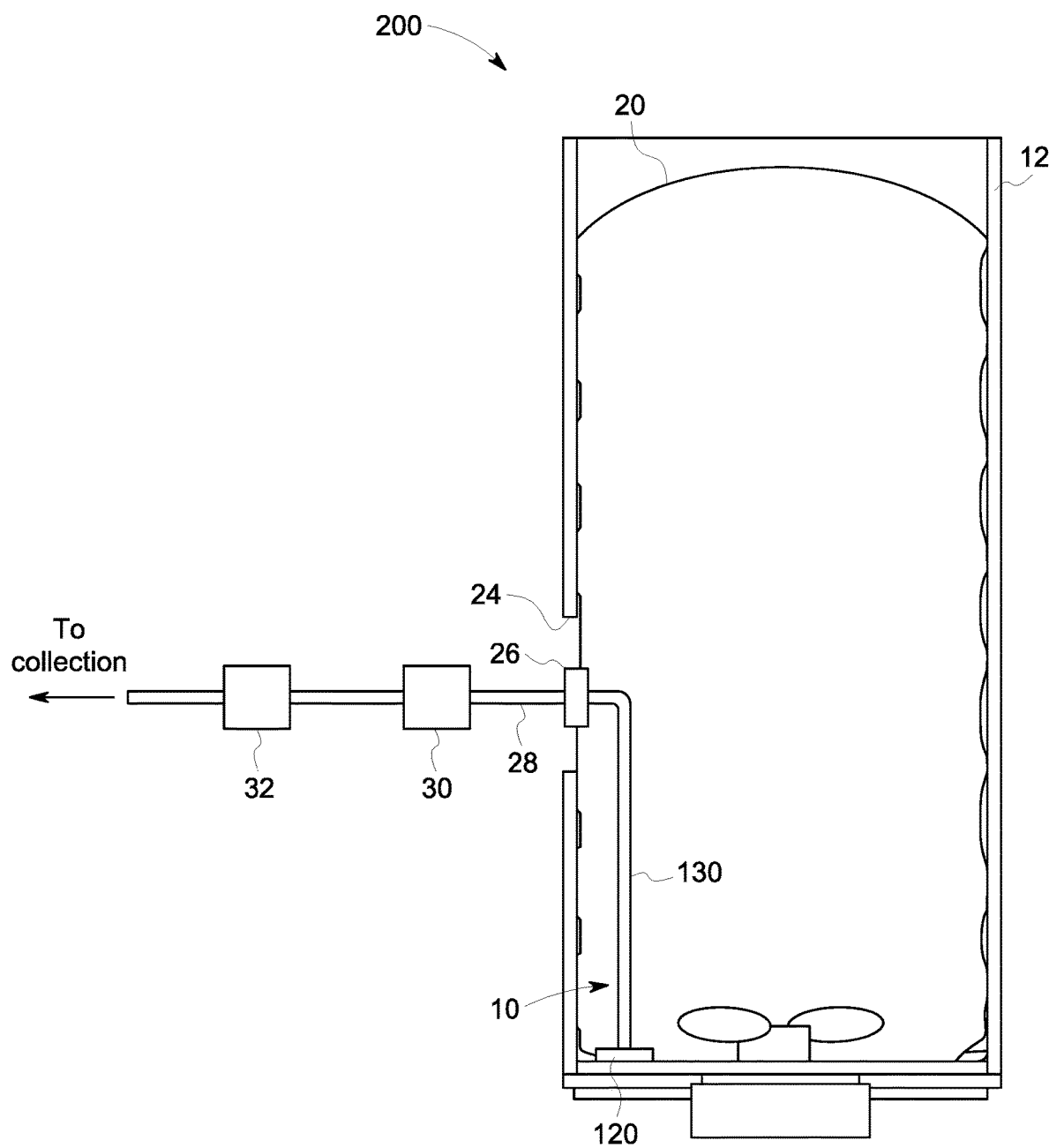
FIG. 8 is a schematic illustration of a suction drain system according to an embodiment of the invention.

With reference to FIG. 8, a second, opposite end of the suction tube 130 is connected to a standard double-sided bag port (e.g., bag port 26 in FIGS. 1 and 8) higher up in the bag wall. In an embodiment, as shown in FIGS. 1 and 8, the bag port 26 may be positioned so as to be accessible through the window 24 in the sidewall of the vessel 12 when the flexible bag 20 is positioned within the vessel 12. As shown therein, the suction tube 130 extends substantially vertically within the flexible bag 20, which is desirable for the reasons presented hereinafter. External tubing 28 can then be connected to the bag at this port (i.e., bag port 26). This external tubing 28 is connected to a pump 30 (e.g., a peristaltic pump), and from there to one or more filters (e.g., filter 32) and other components typically connected to a drain or harvest line. As illustrated in FIG. 8, therefore, a bioprocessing system 200 may include the flexible bioprocessing bag 20 positioned within the vessel 12, and a suction drain system which includes, at least, the apparatus 10 described above, including the suction tube 130 connected to a port 26 in the sidewall of the flexible bag 20, as well as external tubing fluidly coupled to an opposing side of the port 26, and the peristaltic pump 30 for pumping the contents out of the flexible bag 20 for harvesting or draining.

Figure 9:
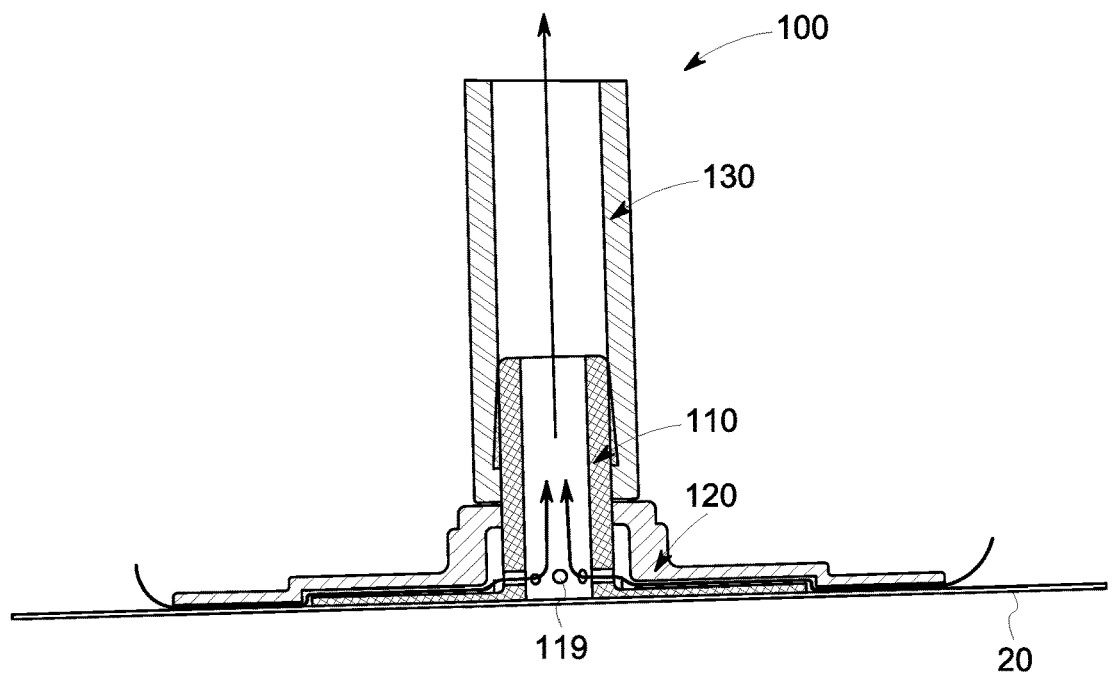
FIG. 9 is a cross-sectional view of the apparatus of FIG. 2, illustrating operation thereof.

As illustrated in FIG. 9, in operation, when draining of the bag 20 is desired, the pump 30 is activated, which causes the fluid within the bag 20 to be drawn through the channels 128 in the underside of the drain flange 120. The fluid is permitted, via the channels 128, to pass through between the drain flange 120 and the upper surface of the flange 112 of the drain port 110, as illustrated by the arrows in FIG. 9. The fluid then passes through the apertures 119 in the tubular body portion 114 of the drain port 110, into the interior passageway 116, and into the suction tube 130. From the suction tube 130, the fluid is drawn out of the flexible bag 20 through the port 26 in the sidewall of the flexible bag 20. As will be appreciated, therefore, the function of the flexible silicone drain flange 120 is to provide thin or narrow passageways (via the channels 128) between the bag film and the drain flange 120. These channels 128 ensure that substantially all of the fluid can be drained from the flexible bag 20.

The apparatus 10 of the invention allows for draining of the flexible bag through a drain line exiting through the sidewall of the flexible bag and through a sidewall of the bioreactor vessel, rather than through a drain line exiting from the bottom of the bag and bottom of the vessel. This configuration facilitates easier and more ergonomic draining of the bioreactor vessel than existing bottom-draining vessels. In particular, prior to the invention described herein, users have been required to reach under the vessel to manipulate drain lines and valves during installation, draining and bag removal. These cumbersome steps have been obviated by the configuration of the apparatus 10 of the invention.

In addition to providing for a more ergonomic means of draining the vessel, the apparatus 10 and system 200 of the invention provide for a number of additional operational advantages. For example, when the external drain tubing 28 is in the peristaltic pump head, the pump 30 acts as a clamp and does not allow air to escape the tubing. This air remains trapped in the suction tube 130 inside the flexible bag 20 and prevents fluid from rising up the drain line when the flexible bag 20 is full of fluid (e.g., during cell culturing or other bioprocessing operations). In an embodiment, the pump 30 may be run in reverse continually or intermittently for a short amount of time (e.g., a couple revolutions) to pump a small volume of air back into the suction tube 130, thus purging any liquid from the drain line 28 or suction tube 130 that may have leaked in. This obviates the need to have a valve at the end of the suction tube 130 where the fluid enters the suction tube 130. In particular, the system 200 is configured such that the pump 30 can create and maintain an air block in the drain line 28 and suction tube 130, which prevents media and cells from entering the suction tube 130 until draining or harvest.

Figure 10:
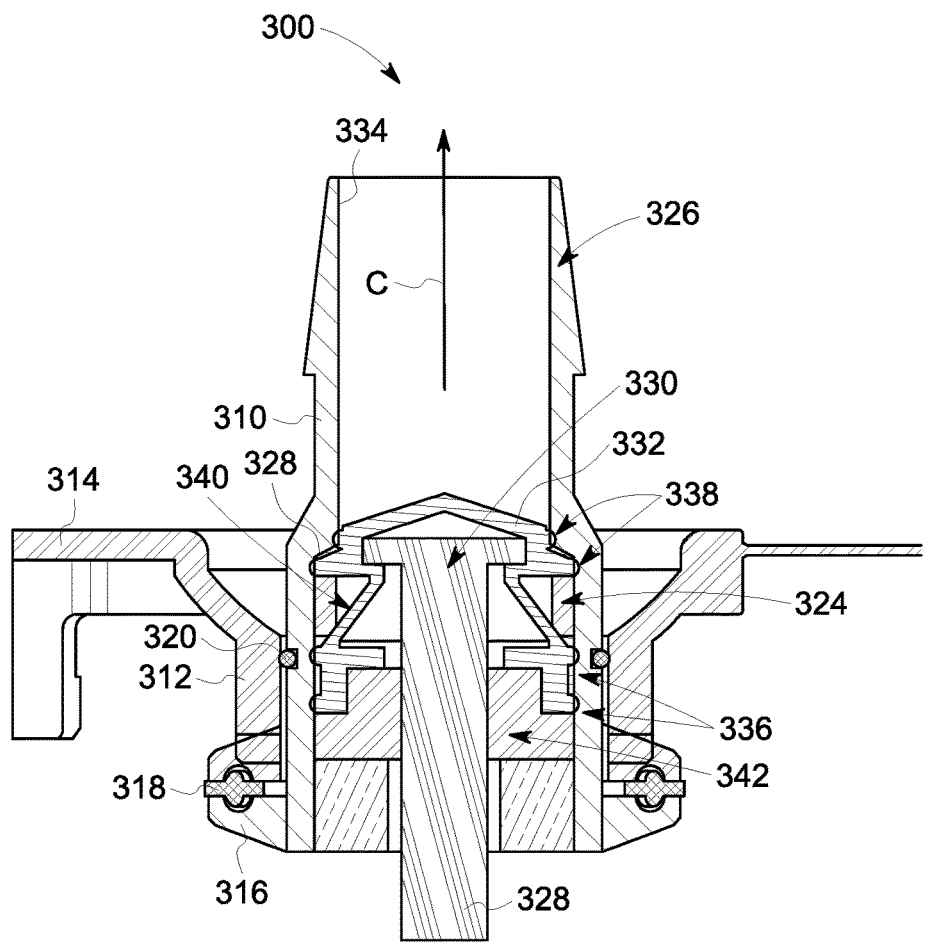
FIG. 10 is a cross-sectional illustration of an apparatus for draining a bioreactor vessel, according to another embodiment of the invention.
Figure 11:
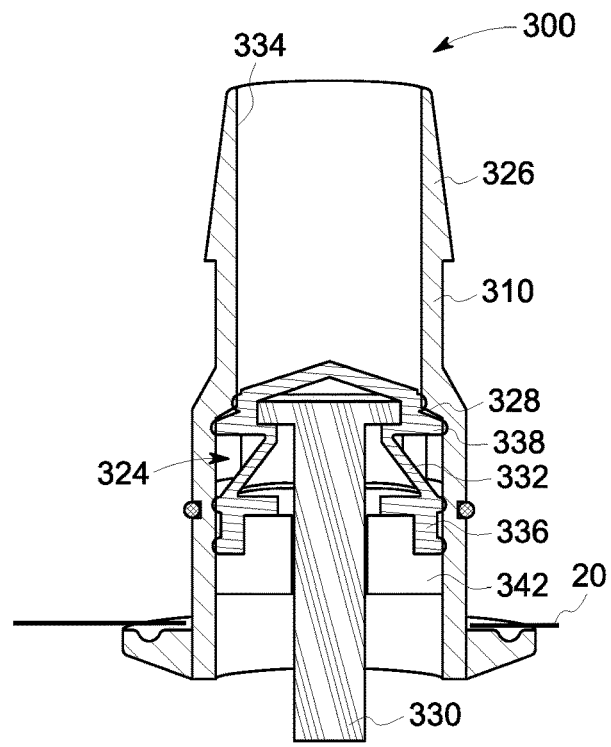
FIG. 11 is a cross-sectional view of the apparatus of FIG. 10, illustrating a closed position.
Figure 12:
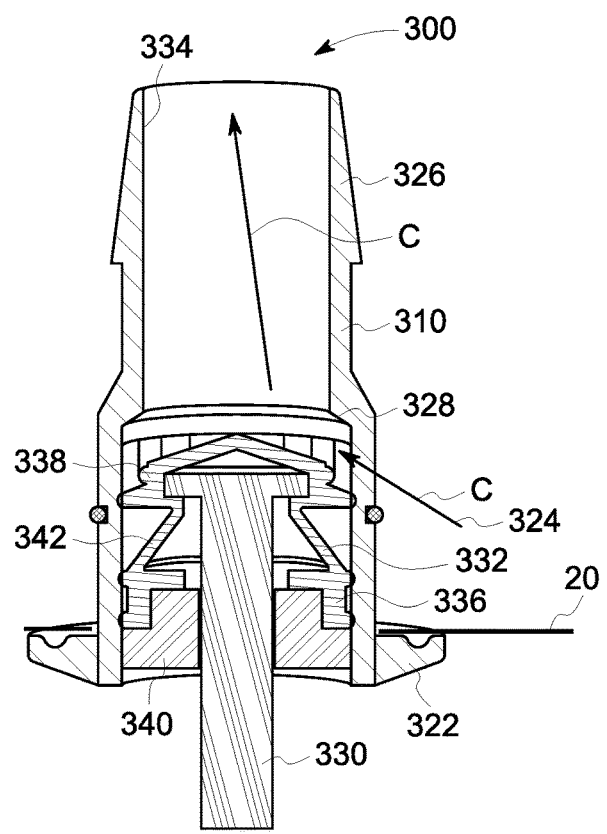
FIG. 12 is a cross-sectional view of the apparatus of FIG. 10, illustrating an open position.

Referring now to FIGS. 10-12, an apparatus 300 for draining a flexible bioreactor bag, e.g., flexible bioreactor bag 20, according to another embodiment of the invention is illustrated. The apparatus 300 is configured to be integrated with the flexible bag 20 for draining of the contents of the bag 20 and includes 100 includes a generally hollow, tubular body portion 310 that extends through an opening in the bottom of the flexible bag 20. As discussed below, various means may be utilized to mount the tubular body portion 310 within the opening in the flexible bag 20.

For example, as illustrated in FIG. 10, in an embodiment, the apparatus 300 may include a drain opening fitting 312 having a flange 314 that is sealingly attached to the inner surface of the flexible bag 20, such as by welding, although other means of attachment may also be utilized without departing from the broader aspects of the invention. The tubular body portion 310 extends through the fitting 312 and is attached to the fitting by a coupling member 316 having a seal 318. A seal element 320 such as, for example, an O-ring disposed in a peripheral groove in the tubular body portion 310 may provide a redundant seal between the tubular body portion 312 and the drain opening fitting 312. As shown in FIG. 10, the drain opening fitting 312 is generally cup-shaped, defining a low point in the flexible bag 20 which facilitates draining of the entire contents of the flexible bag 20.

With specific reference to FIGS. 11 and 12, in another embodiment, the tubular body portion 310 may be secured to the flexible bag 20 via a flange 322 that is sealing attached (e.g., by welding) to an inside or outside surface of the flexible bag 20.

Regardless of the manner in which the apparatus 300 is mounted within the opening in the bottom of the flexible bag 20, the tubular body portion 310 includes one or more apertures or openings 324 in a peripheral sidewall thereof, providing fluid communication between the interior of the flexible bag 20 and the hollow interior of the tubular body portion 310. The tubular body portion 310 also includes a fitting, such as a hose-barb fitting 326, for the connection of suction drain tubing (not shown) to the tubular body portion 310. As shown in FIGS. 10-12, the tubular body portion 310 has a stepped interior passageway 334 having a lower portion having a first diameter, an upper portion having a second diameter that is less than the first diameter, and a step or shoulder 328 forming a transition between the lower portion and the upper portion. As shown therein, the opening 324 are located just below the shoulder 328.

With further reference to FIGS. 10-12, the apparatus 300 further includes a plunger 330 that is slidably received within the tubular body portion 310. The plunger 330 includes a sealing head 332 located on an upper end thereof, which includes a first, lower sealing member 336 configured to sealingly engage the interior sidewall of the lower portion of the interior passageway 334, and a second, upper sealing member 338. The first sealing member 336 and the second sealing member 338 are interconnected by a flexible or resilient membrane 340. In an embodiment, the lower sealing member 336 is configured as a double sealing member have two peripheral sealing elements that are configured to sealingly engage the interior sidewall of the lower portion of the tubular body portion 310. In an embodiment, the upper sealing member 338 is configured as a staggered double sealing member having two stepped or staggered sealing elements, configured to engage the area of the interior passageway 334 about the shoulder 328, as discussed below.

As also shown in FIGS. 10-12, in an embodiment, the apparatus 300 may include a plunger shaft guide 342 received within the lower portion of the passageway 334 and receiving the shaft of the plunger 330 therethrough. The plunger shaft guide 342 is configured to maintain smooth vertical travel of the plunger 330 and sealing head 332 within the tubular body portion 310.

With reference to FIGS. 11 and 12, the plunger 330 and sealing head 332 is moveable between a closed position (FIG. 11) and an open position (FIG. 12). In the closed position, the sealing head 332 is in its upper-most position, with the lower sealing element of the upper sealing member 338 contacting the sidewall of the lower portion of the interior passageway 334, and the upper sealing element of the upper sealing member 338 contacting the sidewall of the upper portion of the interior passageway 334. In this position, the sealing elements of the lower sealing member 336 contact the interior sidewall of the lower portion of the interior passageway 334. In this position, fluid communication between the interior of the flexible bag 20 and the upper portion of the interior passageway 334 is prevented by the upper sealing member 338.

In the open position, as shown in FIG. 12, the upper sealing member 338 is displaced from the shoulder 328 such that the lower sealing element of the upper sealing member 338 sits at a position generally below the openings 324 in the tubular body portion 310, enabling fluid communication between the interior of the flexible bag 20 and the upper portion of the interior passageway 334. In an embodiment, the lower sealing member 336 maintains a fixed position with respect to the tubular body portion 310 when the plunger is moved from the closed position to the open position. This is possible because of the flexible membrane 342, which allows the plunger 330 and the upper sealing member 338 to be moved downwardly, compressing the flexible membrane 338, without transmitting such downward force to the lower sealing member 336.

Figure 13:
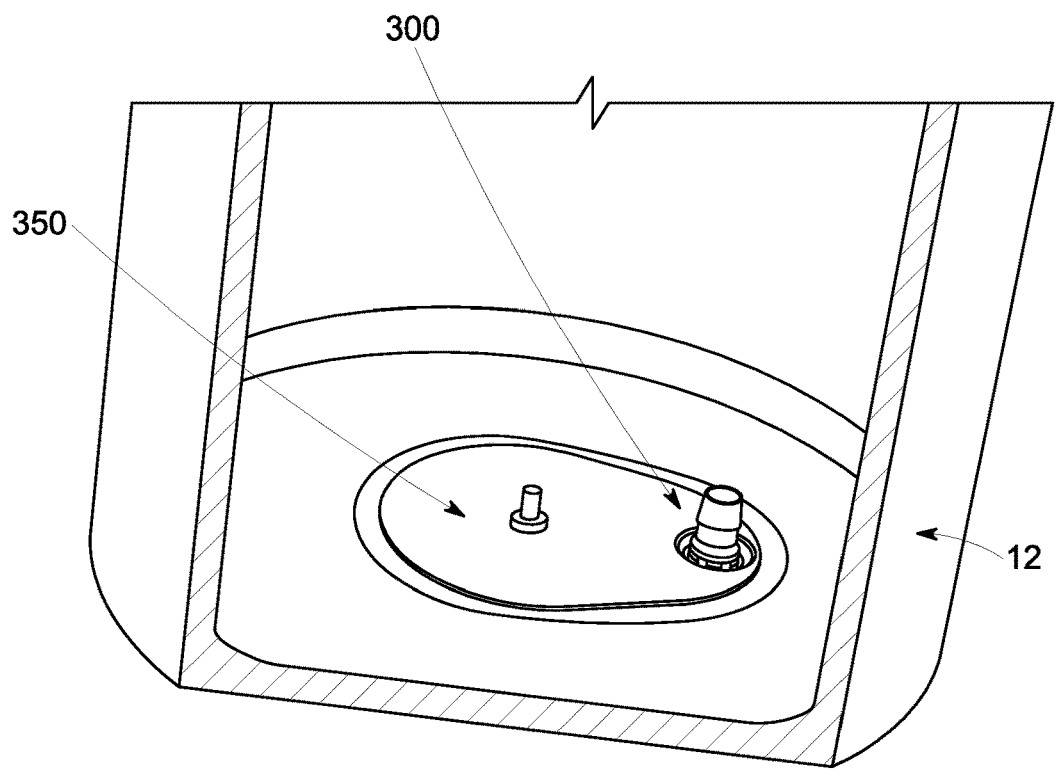
FIG. 13 is a simplified, perspective view of the apparatus in place in a bioprocessing vessel.
Figure 14:
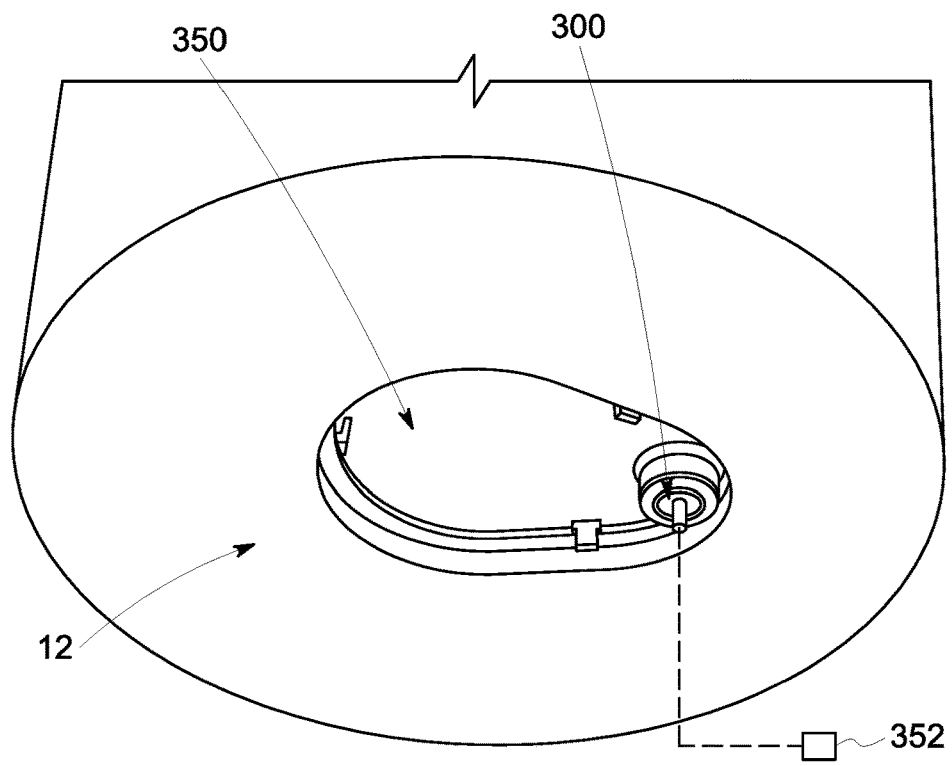
FIG. 14 is another simplified, perspective view of the apparatus in place in a bioprocessing vessel.

FIGS. 13 and 14 illustrate the apparatus 300 in position at the bottom of the bioreactor vessel once the flexible bag 20 is positioned therein. As shown, the apparatus 300 extends through the impeller base plate 350 and a lower end of the plunger 330 protrudes from the bottom of the vessel 12. In an embodiment, the lower end of the plunger 330 of the apparatus 300 is connected to an actuator 352 which is configured to move the plunger vertically between the open and closed positions. The actuator 352 may be, for example, a solenoid, mechanical lever, pneumatic cylinder, although other mechanisms capable of imparting vertical movement to the plunger 330 may also be utilized without departing from the broader aspects of the invention.

In use, the flexible bag 20 is placed within the bioreactor vessel 12 such that the plunger 330 of the suction drain apparatus 300 extends through an opening in the bottom of the bioreactor vessel 12. The actuator 352 is then connected to the plunger 330. The tubular body portion 310 of the apparatus 300 is then connected to a suction drain system, as described above in connection with FIG. 8. In particular, during fabrication of the bag 20, a first end of the suction tube 130 is connected to the tubular body portion 310 of the apparatus via the hose barb connector 326, and a second, opposite end of the suction tube 130 is connected to a standard double-sided bag port (e.g., bag port 26 in FIGS. 1 and 8) higher up in the bag wall. In an embodiment, as shown in FIGS. 1 and 8, the bag port 26 may be positioned so as to be accessible through the window 24 in the sidewall of the vessel 12 when the flexible bag 20 is positioned within the vessel 12. As shown therein, the suction tube 130 extends substantially vertically within the flexible bag 20, which is desirable for the reasons presented hereinafter. External tubing 28 can then be connected to the bag at this port (i.e., bag port 26) in the field. This external tubing 28 is connected to a pump 30 (e.g., a peristaltic pump), and from there to one or more filters (e.g., filter 32) and other components typically connected to a drain or harvest line.

In operation, when draining of the bag 20 is desired, the actuator 352 is utilized to move the plunger downwardly, moving the upper sealing member 338 from its seated position on the shoulder 328. As the lower sealing element of the upper sealing member 338 is moved to a location below the openings 324 in the tubular body portion 310, fluid from within the bag 20 is permitted to pass into the passageway 334. When the suction pump, e.g., peristaltic pump 30 is activated, the fluid within the bag 20 to be drawn through the openings 324 in the tubular body portion 310, into the interior passageway 334, as illustrated by the arrows, C, in FIGS. 10 and 12, and into the suction tube 130. From the suction tube 130, the fluid is drawn out of the flexible bag 20 through the port 26 in the sidewall of the flexible bag 20.

The staggered seal of the upper sealing member 338 provides both redundancy, ensuring that the seal does not leak, and a way to shorten the stroke or vertical movement of the plunger 330. In particular, if both sealing elements of the upper sealing member 338 were the same diameter, the entire sealing member 338 would have to be moved below the openings 324 to expose the openings to the interior passageway 334. In contrast, the staggered double seal configuration of the upper sealing member 338 allows both seals to be opened simultaneously with a much shorter stroke of the plunger.

It is contemplated that the actuator 352 may take a variety of different forms. In addition to those described above, in an embodiment, it is contemplated that the actuator 352 may be a valve actuator incorporating a memory shape wire such as Nitinol, which could be disposable along with the flexible bag 20 and configured for single use. In such a case, only a two wire electrical connection would have to be made beneath the bioreactor vessel after installing the bag. In an embodiment, a power transfer system based on electrical induction may be utilized, in which case a transmitting coil can be permanently mounted under the vessel 12, and a receiving coil could form part of the disposable valve actuator (integrated with the disposable bag 20). The inductive coupling could supply power to the disposable actuator to eliminate the need for a user having to reach under the vessel to connect the actuator.

The apparatus 300 of the invention therefore allows for draining of the flexible bag through a drain line exiting through the sidewall of the flexible bag and through a sidewall of the bioreactor vessel, rather than through a drain line exiting from the bottom of the bag and bottom of the vessel. This configuration facilitates easier and more ergonomic draining of the bioreactor vessel than existing bottom-draining vessels. In particular, prior to the invention described herein, users have been required to reach under the vessel to manipulate drain lines and valves during installation, draining and bag removal. These cumbersome steps have been obviated by the configuration of the apparatus 300 of the invention. As will be appreciated, the suction drain devices described herein also eliminate dead leg spaces that are typically present with existing bottom-draining systems (i.e., dead leg spaces are formed by the drain tubing that extends downwardly from the bottom of the flexible bag.

In an embodiment, an apparatus for draining a bioreactor vessel is provided. The apparatus includes a tubular body portion having an interior passageway, and at least one aperture in the tubular body portion providing for fluid communication with the interior passageway, the tubular body portion being configured for positioning at a bottom of a vessel, and a suction tube having a first end configured for fluid coupling with the tubular body portion, and a second end configured for fluid coupling with a port in a sidewall of the vessel. In an embodiment, the vessel is a flexible bioprocessing bag. In an embodiment, the apparatus also includes a drain flange positionable over the tubular body portion, whereby when positioned over the tubular body portion, the drain flange defines a space between the bottom of the vessel and the drain flange for passage of a fluid between the drain flange and the bottom of the vessel and into the at least one aperture in the tubular body portion. In an embodiment, the tubular body portion includes a flange portion configured for attachment to the bottom of the vessel, and the at least one aperture is located in the tubular body portion above an upper surface of the flange portion. In an embodiment, the drain flange includes a plurality of radially extending channels in a bottom surface of the flange, wherein the plurality of channels provide fluid communication between an interior of the vessel and the at least one aperture in the tubular body portion. In an embodiment, the drain flange includes a neck defining a passageway for receiving the tubular body portion therethrough. In an embodiment, the tubular body portion includes a hose barb connector for connecting the suction tube to the tubular body portion. In an embodiment, the at least one aperture is a plurality of radial apertures disposed about a periphery of the tubular body portion. In an embodiment, the apparatus also includes a plunger slidably received within the interior passageway of the tubular body portion, wherein the plunger is movable between a closed position where there is no fluid communication between the at least one opening and the suction tube, and an open position where the at least one opening is in fluid communication with the suction tube. In an embodiment, the interior passageway has a lower portion having a first diameter, an upper portion having a second diameter that is less than the first diameter, and a shoulder forming a transition between the lower portion and the upper portion forming a stepped area of the interior passageway, and the plunger includes a sealing head having a stepped sealing member corresponding to the stepped area of the interior passageway. In an embodiment, the stepped sealing member has an upper sealing element configured to form a seal with the upper portion of the interior passageway when the plunger is in the closed position, and a lower sealing element configured to form a seal with the lower portion of the interior passageway when the plunger is in the closed position. In an embodiment, the sealing head includes a lower sealing member having at least one sealing element forming a seal with the lower portion of the interior passageway and a flexible membrane joining the stepped sealing member and the lower sealing member. In an embodiment, the lower sealing member maintains a fixed position within the interior passageway. In an embodiment, the lower sealing element includes at least two sealing elements. In an embodiment, the apparatus also includes an actuator configured to move the plunger between the closed position and the open position.

In another embodiment, a bioprocessing apparatus is provided. The bioprocessing apparatus includes a flexible bioprocessing bag, and an apparatus for draining the flexible bioprocessing bag positioned at a bottom of the flexible bioprocessing bag. The apparatus includes a tubular body portion having an interior passageway, and at least one aperture in the tubular body portion providing for fluid communication with the interior passageway, the tubular body portion being configured for positioning at a bottom of a flexible bioprocessing bag. The apparatus also includes a suction tube having a first end configured for fluid coupling with the tubular body portion, and a second end configured for fluid coupling with a port in a sidewall of the flexible bioprocessing bag. In an embodiment, the apparatus further includes a drain flange positionable over the tubular body portion, whereby when positioned over the tubular body portion, the drain flange defines a space between the bottom of the flexible bioprocessing bag and the drain flange for passage of a fluid between the drain flange and the bottom of the flexible bioprocessing bag and into the at least one aperture in the tubular body portion. In an embodiment, the tubular body portion includes a flange portion configured for attachment to the bottom of the flexible bioprocessing bag, and the at least one aperture is located in the tubular body portion above an upper surface of the flange portion. In an embodiment, the drain flange includes a plurality of radially extending channels in a bottom surface of the flange, wherein the plurality of channels provide fluid communication between an interior of the flexible bioprocessing bag and the at least one aperture in the tubular body portion. In an embodiment, the apparatus also includes a plunger slidably received within the interior passageway of the tubular body portion, wherein the plunger is movable between a closed position where there is no fluid communication between the at least one opening and the suction tube, and an open position where the at least one opening is in fluid communication with the suction tube. In an embodiment, the interior passageway has a lower portion having a first diameter, an upper portion having a second diameter that is less than the first diameter, and a shoulder forming a transition between the lower portion and the upper portion forming a stepped area of the interior passageway, and the plunger includes a sealing head having a stepped sealing member corresponding to the stepped area of the interior passageway. In an embodiment, the stepped sealing member has an upper sealing element configured to form a seal with the upper portion of the interior passageway when the plunger is in the closed position, and a lower sealing element configured to form a seal with the lower portion of the interior passageway when the plunger is in the closed position. In an embodiment, the sealing head includes a lower sealing member having at least one sealing element forming a seal with the lower portion of the interior passageway and a flexible membrane joining the stepped sealing member and the lower sealing member. In an embodiment, the lower sealing member maintains a fixed position within the interior passageway. In an embodiment, the bioprocessing system also includes an actuator configured to move the plunger between the closed position and the open position. In an embodiment, the bioprocessing system may also include an external drain tube connected to the port from an exterior side of the flexible bag and a peristaltic pump in engagement with the external drain tube. In an embodiment, the peristaltic pump is operable in a first mode wherein fluid is drawn from the interior of the flexible bioprocessing bag, through the space between the bottom of the flexible bioprocessing bag and the drain flange, into the interior passageway of the tubular body portion via the at least one aperture, through the suction tube and out of the flexible bioprocessing bag through the port, and a second mode wherein the peristaltic pump is operated in reverse to pump air into the suction tube to maintain an air block within the suction tube to prevent the fluid from entering the suction tube. In an embodiment, the port in the sidewall of the flexible bioprocessing bag is accessible through a window in a sidewall of the flexible bioprocessing bag. In an embodiment, the tubular body portion includes a flange portion configured for attachment to the bottom of the flexible bioprocessing bag, and wherein the at least one aperture is located in the tubular body portion above an upper surface of the flange portion.

In yet another embodiment, a method of draining a flexible bioprocessing bag is provided. The method includes the steps of arranging a suction tube interior to a flexible bioprocessing bag such that a first end of the suction tube is connected to a suction drain device attached to a bottom of the flexible bioprocessing bag and a second end of the suction tube is connected to a port in a sidewall of the flexible bioprocessing bag, changing a state of the suction drain device to place an interior of the flexible bioprocessing bag in fluid communication with the suction tube, and activating a pump to draw a fluid from the interior of the flexible bioprocessing bag into the suction tube and out of the flexible bioprocessing bag through the port in the sidewall of the flexible bioprocessing bag. In an embodiment, the suction drain device includes a tubular body portion having an interior passageway, and at least one aperture in the tubular body portion providing for fluid communication with the interior passageway, the tubular body portion being configured for positioning at a bottom of the flexible bioprocessing bag, wherein the first end of the suction tube is connected to the tubular body portion. In an embodiment, the suction drain device includes a drain flange positionable over the tubular body portion, whereby when positioned over the tubular body portion, the drain flange defines a space between the bottom of the vessel and the drain flange for passage of a fluid between the drain flange and the bottom of the vessel and into the at least one aperture in the tubular body portion. In an embodiment, the suction drain device includes a plunger slidably received within the interior passageway of the tubular body portion, wherein the plunger is movable between a closed position where there is no fluid communication between the at least one opening and the suction tube, and an open position where the at least one opening is in fluid communication with the suction tube.

In yet another embodiment, a bioprocessing system is provided. The bioprocessing system includes a vessel. a flexible bioprocessing bag positionable within the vessel, and an apparatus for draining the flexible bioprocessing bag positioned at a bottom of the flexible bioprocessing bag. The apparatus includes a tubular body portion having an interior passageway, and at least one aperture in the tubular body portion providing for fluid communication with the interior passageway, the tubular body portion being configured for positioning at a bottom of a flexible bioprocessing bag. The apparatus also includes a suction tube having a first end configured for fluid coupling with the tubular body portion, and a second end configured for fluid coupling with a port in a sidewall of the flexible bioprocessing bag. In an embodiment, the apparatus further includes a drain flange positionable over the tubular body portion, whereby when positioned over the tubular body portion, the drain flange defines a space between the bottom of the flexible bioprocessing bag and the drain flange for passage of a fluid between the drain flange and the bottom of the flexible bioprocessing bag and into the at least one aperture in the tubular body portion. In an embodiment, the tubular body portion includes a flange portion configured for attachment to the bottom of the flexible bioprocessing bag, and the at least one aperture is located in the tubular body portion above an upper surface of the flange portion. In an embodiment, the drain flange includes a plurality of radially extending channels in a bottom surface of the flange, wherein the plurality of channels provide fluid communication between an interior of the flexible bioprocessing bag and the at least one aperture in the tubular body portion. In an embodiment, the apparatus also includes a plunger slidably received within the interior passageway of the tubular body portion, wherein the plunger is movable between a closed position where there is no fluid communication between the at least one opening and the suction tube, and an open position where the at least one opening is in fluid communication with the suction tube.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for draining a bioreactor, comprising:
   a tubular body portion having an interior passageway, at least one aperture in the tubular body portion providing for fluid communication with the interior passageway, and a flange portion configured for attachment to a bottom of a vessel, the at least one aperture being located in the tubular body portion above an upper surface of the flange portion;
   a drain flange positionable over the tubular body portion and the flange portion of the tubular body portion, whereby when positioned over the tubular body portion, the drain flange extends over the upper surface and a side surface of the flange portion of the tubular body portion, and beyond a periphery of the side surface to extend over a portion of the bottom of the vessel, the positioning of the drain flange over the flange portion of the tubular body portion defining a first space between the bottom of the vessel and a bottom surface of the drain flange, and a second space between the upper surface and side surface of the flange portion of the tubular body portion and the bottom surface of the drain flange, the first space and the second space in fluid communication, wherein the first space and the second space delineate a drainage passage for a flow of a fluid from the bottom of the vessel to between the drain flange and the bottom of the vessel, to between the drain flange and the flange portion of the tubular body portion, and into the at least one aperture in the tubular body portion; and
   a suction tube having a first end configured for fluid coupling with the tubular body portion, and a second end configured for fluid coupling with a port in a sidewall of the vessel.

2. The apparatus of claim 1, wherein:
   the vessel is a flexible bioprocessing bag.

3. The apparatus of claim 1, wherein:
   the drainage passage comprises a plurality of radially extending channels in the bottom surface of the drain flange;
   wherein the plurality of channels provide fluid communication between an interior of the vessel and the at least one aperture in the tubular body portion.

4. A bioprocessing apparatus, comprising:
   a flexible bioprocessing bag; and
   an apparatus for draining the flexible bioprocessing bag positioned at a bottom of the flexible bioprocessing bag, the apparatus including:
   a tubular body portion having an interior passageway, at least one aperture in the tubular body portion providing for fluid communication with the interior passageway, and a flange portion configured for attachment to a bottom of a flexible bioprocessing bag, the at least one aperture being located in the tubular body portion above an upper surface of the flange portion;
   a drain flange positionable over the tubular body portion and the flange portion of the tubular body portion, whereby when positioned over the tubular body portion, the drain flange extends over the upper surface and a side surface of the flange portion of the tubular body portion, and beyond a periphery of the side surface to extend over a portion of the bottom of the bioprocessing bag, the positioning of the drain flange over the flange portion of the tubular body portion defining a first space between the bottom of the bioprocessing bag and a bottom surface of the drain flange, and a second space between the upper surface and side surface of the flange portion of the tubular body portion and the bottom surface of the drain flange, the first space and the second space in fluid communication, wherein the first space and the second space delineate a drainage passage for a flow of a fluid from the bottom of the bioprocessing bag to between the drain flange and the bottom of the bioprocessing bag, to between the drain flange and the flange portion of the tubular body portion, and into the at least one aperture in the tubular body portion; and
   a suction tube having a first end configured for fluid coupling with the tubular body portion, and a second end configured for fluid coupling with a port in a sidewall of the flexible bioprocessing bag.

5. The bioprocessing system of claim 4, wherein:
   the drainage passage comprises a plurality of radially extending channels in the bottom surface of the drain flange;
   wherein the plurality of channels provide fluid communication between an interior of the flexible bioprocessing bag and the at least one aperture in the tubular body portion.

6. The bioprocessing system of claim 4, further comprising:
   an external drain tube connected to the port from an exterior side of the flexible bag; and
   a peristaltic pump in engagement with the external drain tube.

7. The bioprocessing system of claim 6, wherein:
   the peristaltic pump is operable in a first mode wherein fluid is drawn from the interior of the flexible bioprocessing bag, through the space between the bottom of the flexible bioprocessing bag and the drain flange, into the interior passageway of the tubular body portion via the at least one aperture, through the suction tube and out of the flexible bioprocessing bag through the port, and a second mode wherein the peristaltic pump is operated in reverse to pump air into the suction tube to maintain an air block within the suction tube to prevent the fluid from entering the suction tube.

8. An apparatus for draining a bioreactor, comprising:
   a drain flange positioned about a drain opening in a bottom of a vessel;

a tubular body portion extending through the drain flange and the drain opening, the tubular body portion having an interior passageway, and at least one aperture in a peripheral sidewall of the tubular body portion providing for fluid communication with the interior passageway, the interior passageway having a lower portion proximate the drain flange and the drain opening with a first diameter, an upper portion distal to the drain flange and the drain opening with a second diameter that is less than the first diameter, and a shoulder forming a transition between the lower portion and the upper portion that defines a stepped area of the interior passageway, the at least one aperture located below the shoulder;

a suction tube having a first end configured for fluid coupling with the tubular body portion, and a second end configured for fluid coupling with a port in a sidewall of the vessel; and a plunger slidably received within the interior passageway of the tubular body portion, wherein the plunger movable between a closed position where there is no fluid communication between the at least one aperture and the suction tube and an open position where the at least one aperture is in fluid communication with the suction tube, wherein the plunger includes a sealing head configured to sealingly engage an interior sidewall of the interior passageway of the tubular body portion, the sealing head sealingly engaging with the interior sidewall of the interior passageway adjacent the shoulder when the plunger is in the closed position and sealingly engaging with the interior sidewall of the interior passageway below the shoulder at the lower portion of the interior passageway when the plunger is in the open position, wherein the sealing head is shaped to correspond with the stepped area of the interior passageway, wherein the sealing head includes a peak portion, an upper sealing element below the peak portion, a lower sealing element beneath the upper sealing element, and a flexible membrane interconnecting the upper sealing element with the lower sealing element, the upper sealing element having a base sealing element and a top sealing element, the base sealing element and the top sealing element defining a stepped arrangement of the sealing elements that ascends towards the peak portion, wherein the peak portion and the top sealing element are below the shoulder of the interior passageway and the top sealing element is unengaged from the interior sidewall when the plunger is in the open position to permit fluid communication with the interior passageway, while the base sealing element forms a seal with the interior sidewall in the lower portion of the interior passageway, wherein the top sealing element forms a seal with the interior sidewall of the interior passageway in the upper portion adjacent the shoulder with the peak portion extending above the shoulder when the plunger is in the closed position, while the base sealing element forms a seal with the interior sidewall of the interior passageway in the lower portion adjacent the shoulder.

9. The apparatus of claim 8, wherein:
the lower sealing element includes at least one sealing element forming a seal with the interior sidewall of the interior passageway at the lower portion thereof.

10. The apparatus of claim 9, wherein the lower sealing element comprises a first sealing element and a second sealing element spaced apart and below the first sealing element, the second sealing element in vertical alignment with the first sealing element, wherein both the first sealing element and the second sealing element form a seal with the interior sidewall of the interior passageway.

11. The apparatus of claim 8, wherein the flexible membrane is sloped from a surface of the base sealing element of the upper sealing element away from the plunger towards a surface of the lower portion.

\* \* \* \* \*